United States Patent [19]
Chen

[11] Patent Number: 4,618,213

[45] Date of Patent: * Oct. 21, 1986

[54] GELATINOUS ELASTOMERIC OPTICAL LENS, LIGHT PIPE, COMPRISING A SPECIFIC BLOCK COPOLYMER AND AN OIL PLASTICIZER

[75] Inventor: John Y. Chen, Pacifica, Calif.

[73] Assignee: Applied Elastomerics, Incorporated, Pacifica, Calif.

[*] Notice: The portion of the term of this patent subsequent to Jan. 18, 2000 has been disclaimed.

[21] Appl. No.: 572,172

[22] Filed: Jan. 18, 1984

Related U.S. Application Data

[63] Continuation-in-part of Ser. No. 458,703, Jan. 17, 1983, abandoned, which is a continuation-in-part of Ser. No. 134,977, Mar. 28, 1980, Pat. No. 4,369,284, said Ser. No. 134,977, is a continuation-in-part of Ser. No. 916,731, Jan. 19, 1978, abandoned, which is a continuation-in-part of Ser. No. 815,315, Jul. 13, 1977, abandoned, which is a continuation-in-part of Ser. No. 778,343, Mar. 17, 1977, abandoned.

[51] Int. Cl.$^4$ .......................... C08K 5/01; G02B 6/00; G02B 5/04
[52] U.S. Cl. .................................. 350/96.34; 350/286; 350/409; 446/385; 446/486; 524/476; 524/505
[58] Field of Search ............... 524/476, 505; 350/409, 350/286, 96.34; 446/385, 486

[56] References Cited

U.S. PATENT DOCUMENTS

| | | | |
|---|---|---|---|
| 2,830,402 | 4/1958 | Schleich | 446/385 |
| 4,136,699 | 1/1979 | Collins et al. | 128/290 R |
| 4,176,240 | 11/1979 | Sabia | 174/23 C |
| 4,259,540 | 3/1981 | Sabia | 524/505 |
| 4,369,284 | 1/1983 | Chen | 524/476 |
| 4,492,428 | 1/1985 | Levy | 524/505 |

FOREIGN PATENT DOCUMENTS 1268431 3/1972 United Kingdom .

Primary Examiner—Herbert J. Lilling

[57] ABSTRACT

A novel gelatinous composition is disclosed which contains an intimate melt blend admixture of poly(styrene-ethylene-butylene-styrene) triblock copolymer having said styrene end block to ethylene and butylene center block ratio within the range of from between 31:69 to 40:60, and high levels of a plasticizing oil.

The gelatinous composition is transparent and have a novel combination of properties including unexpectedly high elongation and tensile strength and excellent shape retention after extreme deformation under high-velocity impact and stress conditions. The gelatinous products of this invention are soft, flexible, and have elastic memory, characterized by a gel rigidity of from about 20 gram to about 700 gram Bloom. These and other properties are particularly essential for the gelatinous composition to have utility as toys, therapeutic hand exercising grips, shock absorbers, acoustical isolators, and other uses.

22 Claims, No Drawings

GELATINOUS ELASTOMERIC OPTICAL LENS, LIGHT PIPE, COMPRISING A SPECIFIC BLOCK COPOLYMER AND AN OIL PLASTICIZER

REFERENCED TO RELATED APPLICATION

This application is a continuation-in-part of copending application Ser. No. 458,703, filed Jan. 17, 1983, which is a continuation-in-part of copending application Ser. No. 134,977, filed Mar. 28, 1980, and issued as U.S. Pat. No. on Jan. 18, 1983; which in turn is a continuation-in-part of my application Ser. No. 916,731, filed June 19, 1978, which is a continuation-in-part of application Ser. No. 815,315, filed July 13, 1977, which is a continuation-in-part of application Ser. No. 778,343, filed Mar. 17, 1977, said applications now abandoned.

The aforementioned application and patent are incorporated herein by reference.

FIELD OF THE INVENTION

The present invention relates to new and particularly, useful gelatinous elastomeric lenses and light conductors such as pipes, tubes, cylinders, rods, and the like. More specifically, the invention is related to transparent gelatinous elastomeric articles that have at least two opposite regular surfaces either both curved or one curved and the other plane and that can be used either singly or combined in an optical instrument or in the hand for forming an image by focusing rays of light, said articles having lens shapes such as plano-convex, bi-convex, converging meniscus, plano-concave, bi-concave, diverging meniscous, cylinderical, and spherical; said articles being highly extensible and strong, extremely soft and flexible, and possess elastic memory.

BACKGROUND OF THE INVENTION

It is well known that thermoplastic elastomers, more particularly, thermoplastic block copolymers can be oil-extended to produce soft and flexible compositions. However, the oil plasticized thermoplastic block copolymer compositions of the prior art suffers from one or more of the poor physical and mechanical properties such as poor breaking strength, poor elongation, poor craze, tear, creep, and crack resistance, and poor oil acceptance, to name a few. For instance, *Shell Technical Bulletin* No. SC 65-75 teaches the use of poly(styrene-ethylene-butylene-styrene) triblock copolymers Shell Kraton G 1650 and G 1652 having styrene end block to ethylene and butylene center block ratio of 28:72 and 29:71 respectively in blends with butyl rubber, tackifier, filler, and oil. However, in none of the blends just described are the properties of the compositions desirable; but rather, the use of other polymers such as butyl rubber, tackifiers, and fillers for extending and plasticizing the triblock copolymers result in dimensionally unstable mastic like materials which are not acceptable for purposes of the present invention. Furthermore, when the triblock copolymers as disclosed in Shell's Bulletin No. SC 65-75 are plasticized with oil, the compositions obtained show decreases in the desired properties such as poor elongation and tensile strength, poor creep, craze, tear, and crack resistance; in addition, these compositions of the prior art tend to rupture and crumble when submitted to moderate shearing stress conditions.

SUMMARY OF THE INVENTION

Accordingly, it is an object of the present invention to provide compositions substantially free of one or more of the disadvantages of prior art compositions.

Another object is to provide gelatinous elastomer compositions which are transparent.

Yet another object is to provide gelatinous elastomer compositions of high dimensional stability, excellent crack, tear, craze, and creep resistance, improved tensile strength and high elongation.

A still further object is to provide gelatinous elastomer compositions having long service life under vibrational stress, and allows for repeated handling.

Another object is to provide gelatinous elastomer compositions having excellent processing ability for cast moulding.

Yet another object is to produce transparent, dimensionally stable, non-toxic, nearly tasteless and odorless, extremely soft, highly flexible, and easily hand deformable moulded gelatinous elastomer articles prossessing elastic memory from compositions of the instant invention.

Another object is to provide transparent gelatinous elastomeric optical lenses and light conducting articles such as rods, tubes, and the like which are extremely soft, highly flexible, easily hand deformable, prosess elastic memory, and other desired properties.

Other objects, aspects and advantages of the invention will become apparent to those skilled in the art upon consideration of the accompanying disclosure.

In accordance with the present invention, I have unexpectedly discovered that a gelatinous elastomer composition having novel combination of properties can be provided by melt blending an admixture consisting essentially of:

(A) 100 parts by weight of a triblock copolymer of the general configuration poly(styrene-ethylene-butylene-styrene) wherein said styrene end block to ethylene and butylene center block ratio is within the range of from between 31:69 to 40:60;

(B) from about 300 to about 1,600 parts by weight of an plasticizing oil selected from the group consisting of petroleum paraffinic oils, petroleum naphthenic oils, sythetic polybutene oils, synthetic polypropene oils, sythetic polyterpene oils and mixtures thereof; said oils having an average molecular weight of between about 200 to about 700.

Preferably, the triblock copolymer contemplated in (A) have a styrene end block to ethylene and butylene center block ratio of about 32:68 to about 38:62, more preferably about 32:68 to about 36:64, particularly more preferably about 32:68 to about 34:66, especially more preferably about 33:67 to about 36:64, and most preferably about 33:67.

The proportion of hydrocarbon plasticizing oil contemplated in (B) is more preferably from about 350 to about 1,600 parts per 100 parts of the triblock copolymer.

The compositions of the instant invention are formed into lenses, light conducting articles and cladding for optical fibers.

DESCRIPTION OF THE PREFERRED EMBODIMENTS

The triblock copolymers employed in the present invention have the more general configuration A-B-A wherein each A is a crystalline polymer end block segment of polystyrene; and B is a elastomeric polymer center block segment of poly(ethylen-butylene). The poly(ethylene-butylene) and polystyrene portions are incompatible and form a two-phase system consisting of sub-micron domains of glassy polystyrene interconnected by flexible poly(ethylene-butylene) chains. These domains serve to crosslink and reinforce the structure. This physical elastomeric network structure is reversible, and heating the polymer above the softening point of polystyrene temporarily disrupt the structure, which can be restored by lowering the temperature.

Plasticizers particularly preferred for use in practicing the present invention are well known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, and polyterpene. The synthetic series process oils are high molecular weight oligomers which are permanently fluid liquid monoolefins, isoparaffins or paraffins of moderate to high viscosity. Many such oils are known and commercially available.

The triblockcopolymer component by itself lacks the desired contemplated properties; whereas, when the triblock copolymer (having styrene to ethylene and butylene ratio within the range contemplated in the instant invention) is combined with selected plasticizing oils with an average molecular weight of between about 200 to about 700, as determined by ebulliscopic methods, wherein, for most purposes, the oil constitutes about 300 to about 1,600 parts and more preferably about 350 to about 1,600 parts by weight of the triblock copolymer, that an extremely soft and highly elastic material is obtained. This transformation of the triblock copolymer structure in heated oil resulting in a composition having a gel rigidity of about 20 gram to about 700 gram Bloom and substantially without oil bleedout along with high tensile strength and elongation and other desirable combination of physical properties is unexpected. As used herein, the term "gel rigidity" in gram Bloom is determined by the gram weight required to depress a gel a distance of 4 mm with a piston having a cross-sectional area of 1 square centimeter at 23° C.

The composition of this invention can also contain small amounts of conventionally employed additives such as stabilizers, antioxidants, antiblocking agents, colorants, fragrances, flame retardants, and the like to an extend not affecting or decreasing the desired properties of the present invention. Additives useful in the compositions of the present invention include: Tetrakis[methylene 3,-(3'5'-di-tertbutyl-4''-hydroxyphenyl)propionate]methane, Octadecyl 3-(3'',5''-di-tert-butyl-4''-hydroxyphenyl)propionate, Distearyl-pentaerythritol-diphosphite, Distearyl-pentaerythritol-diphosphite, Tris(nonyl phenyl)phosphite, 2,6-di-tert-butyl-p-cresol, Dilaurylthiodiproprionate, Thiodiethylene bis-(3,5-tert-butyl-4-hydroxy) hydrocinnamate, (1,3,5-Trimethyl-2,4,6-tris[3,5-di-tert-butyl-4-hydroxybenzyl]benzene), 4,4''-Methylenebis(2,6-di-tert-butylphenol), Stearic Acid, Oleic Acid, Stearamide, Behenamide, Oleamide, Erucamide, N,N'''-ethylenebisstearamide,N,N''-ethylenebisoleamide, Stearyl Erucamide, Erucyl Erucamide, Oleyl Palmitamide, Stearyl Stearamide, Erucyl Stearamide, metallic pigments (aluminum and brass flakes), $TiO_2$, mica, fluorescent dyes and pigments, phosphorescent pigments, aluminatrihydrate, antimony oxide, molybdenum, silicone fluids, lake pigments, aluminates, ceramic pigments, ironblues, ultramarines, phthalocyanines, azo pigments, carbon blacks, silicon dioxide, silica, clay, feldspar, glass microspheres, barium ferrite, wollastonite and the like.

In accordance with the practice of the present invention, the aforementioned molecular weight range plasticizing oils are most preferred. Generally, plasticizing oils with average molecular weights less than about 200 and greater than about 700 may also be used.

The gelatinous elastomer compositions of the present invention are prepared by blending together the components including other additatives as desired at about 23° C. to about 100° forming a paste like mixture and further heating said mixture uniformly to about 150° C. to 200° C. until a homogeneous molten blend is obtained. These components blend easily in the melt and a heated vessel equipped with a stirrer is all that is required.

The instant composition is excellent for cast moulding and the moulded products have various excellent characteristics which cannot be anticipated from the properties of the raw components.

The basis of this invention resides in the fact that a poly(styrene-ethylene-butylene-styrene) triblock copolymer having styrene end block to ethylene and butylene center block ratio within the contemplated range of from between 31:69 to 40:60 when blended in the melt with an appropriate amount of plasticizing oil makes possible the attainment of gelatinous elastomer compositions having a desirable combination of physical and mechanical properties, notably high elongation at break of at least 1,600%, ultimate tensile strength of about at least $8 \times 10^5$ dyne/cm$^2$, low elongation set at break of substantially not greater than about 2%, tear resistance of at least $5 \times 10^5$ dyne/cm$^2$, substantially about 100% snap back when extended to 1,200% elongation, and a gel rigidity of substantially not greater than about 700 gram Bloom. More specifically, the gelatinous compositions of the present invention exhibit one or more of the following properties. These are: (1) tensile strength of about $8 \times 10^5$ dyne/cm$^2$ to about $10^7$ dyne/cm$^2$; (2) elongation of about 1,600% to about 3,000%; (3) elasticity modulus of about $10^4$ dyne/cm$^2$ to about $10^6$ dyne/cm$^2$; (4) shear modulus of about $10^4$ dyne/cm$^2$ to about $10^6$ dyne/cm$^2$ as measured with a 1, 2, and 3 kilogram load at 23° C.; (5) gel rigidity of about 20 gram Bloom to about 700 gram Bloom as measured by the gram weight required to depress a gel a distance of 4 mm with a piston having a cross-sectional area of 1 square cm at 23° C.; (6) tear propagation resistance of at least about $5 \times 10^5$ dyne/cm$^2$; (7) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The gelatinous elastomer articles moulded from the instant compositions have various additional important advantages in that they do not craze, creep, tear, crack, or rupture in flextural, extension, compression, or other deforming conditions of normal use; but rather the moulded articles made from the instant composition possess the intrinsic properties of elastic memory enabling the articles to recover and retain its original moulded shape after many extreme deformation cycles as compared to prior art triblock copolymer oil-extended compositions. In applications where low rigidity, high elongation, good compression set and excellent tensile strength are important, the instant compositions would be preferred.

The gelatinous elastomer compositions of the present invention are useful in low frequency vibration applications, such a viscoelastic layers in constrained-layer damping of mechanical structures and goods, as viscoelastic layers used in laminates for isolation of acoustical and mechanical noise, as viscoelastic layers used in wrappings, enclosures and linings to control sound, as compositions for use in shock and dielectric encapsulations of electrical and electronic components, as moulded shape articles for use as therapeutic hand exercising grips, as articles for use as novel amusement toys, novel re-useable lint removers, optical lenses, light conductors such as pipes, tubes, cylinders, rods, prisms, cones, spheres and the like; other uses may include cladding for optical fibers.

The invention is further illustrated by means of the following illustrative embodiments, which are given for purpose of illustration only and are not meant to limit the invention to the particular reactants and amounts disclosed.

EXAMPLE I

A comparison was made between poly(styrene-ethylene-butylene-styrene) triblock copolymers having styrene end block to ethylene and butylene center block ratio below the range between 31:69 to 40:60 and ratio within the range between 31:69 to 40:60. Three different triblock copolymers were melt blended separately with a paraffinic white petroleum oil. Table I below shows the physical properties obtained with respect to each of the different styrene to ethylene and butylene ratio triblock copolymer oil-blends tested.

The properties were measured as follows:

Tear Propagation (ASTM D 1938 modified)

6 mm by 25 mm by 75 mm strips with a 50 mm longitudinal slit razor cut were tored through the entire unslited 25 mm portion at a crosshead separation speed of 250 mm per minute.

Cracking (ASTM D 518 Method B modified)

25 mm by 50 mm by 150 mm long strips were bent 180° until their ends meet making a loop and placed between clamping blocks. The clamping blocks were compressed together under a constant force of 50 grams and the samples were timed from initial application of the 50 gram force till the first appearance or surface cracking resulting in complete failure due to crack growth in the looped portion of the specimen.

Tensile Strength(ASTM D 412 modified)

6 mm by 25 mm by 100 mm strips were extended at a crosshead separation speed of 508 mm per minute till break.

Ultimate elongation(ASTM D 412 modified)

6 mm by 25 mm by 100 mm strips were extended at a crosshead separation speed of 508 mm per minute till break.

Tensile Set(ASTM D 412 modified)

6 mm by 25 mm by 100 mm strips were mechanically extended at a grip separation speed of 250 mm per minute and maintained at test conditions of 50%, 100%, 300%, 400%, 600%, and 1,200% elongation for a period of 60 seconds and allowed to freely retract for 10 minutes. The extension remaining after this time period expressed as a percentage of the original length was recorded as set.

Compression Set(ASTM D 395 modified)

25 mm by 25 mm by 25 mm cubes were placed in a compression jig with shims under a constant force of 5,000 grams for periods of 60 seconds, 60 minutes, and 24 hours. The compressive force was removed and set was determined after 30 minutes.

Snap Back 25 mm by 25 mm by 150 mm strips were hand extended by gripping the ends to elongation settings of 50%, 100%, 200%, 400%, 800% and 1,200% for 10 seconds and then allowed to snap back. Separate samples were tested at each elongation setting. The measured extension remaining 5 seconds after snap back was used to determine precentage snap back.

Hand kneading (60 seconds)

25 mm by 25 mm by 25 mm cubes were placed in the palm of one hand and kneaded for 60 seconds thereof examined for appearance and dimensional condition.

TABLE I

| Formulation | S/EB Ratio[1] | Weight Parts | | |
|---|---|---|---|---|
| | | A | B | C |
| S-E-B-S[2] | 28:72 | 100 | | |
| S-E-B-S[3] | 29:71 | | 100 | |
| S-E-B-S[4] | 33:67 | | | 100 |
| Paraffinic oil[5] | | 400 | 400 | 400 |
| Stabilizer[6] | | 2.5 | 2.5 | 2.5 |
| Breaking strength,[7] dyne/cm$^2$ | | 4 × 10$^5$ | 4 × 10$^5$ | 4 × 10$^6$ |
| Tear propagation,[8] dyne/cm$^2$ | | 8 × 10$^4$ | 7 × 10$^4$ | 1 × 10$^6$ |
| Elongation at break,[9] % | | 180 | 168 | 1,700 |
| Compression set[10] at 24 hours | | 81%[R] | 77%[R] | 0.0% |
| Rigidity, gram Bloom | | 1,536 | 1,520 | 360 |

[1] Styrene to ethylene and butylene ratio
[2] Shell Kraton G 1650
[3] Shell Kraton G 1652
[4] Shell Kraton G 1651
[5] ARCO prime 200
[6] Irganox 1010
[7] ASTM D 412 modified
[8] ASTM D 1938 modified
[9] ASTM D 412 modified
[10] ASTM D 395 modified
[R] ruptured completely The result of Table I show drastically un-acceptable poor properties of triblock copolymers having styrene to ethylene and butylene ratios below (not within) the contemplated range of the instant invention.

EXAMPLE II

One hundred parts by weight of a poly(styrene-ethylene-butylene-styrene) triblock copolymer (Shell Kraton G 1651) having a styrene end block to ethylene and butylene center block ratio of about 33:67 with 0.1 parts by weight of a stabilizer (Irganox 1010) was melt blended with various quantities of a naphthenic oil (ARCO Tufflo 6024). Samples having the dimensions of 5 cm by 5 cm by 3 cm were cut and measured for gel rigidity on a modified Bloom gelometer as determined by the gram weight required to depress the gel a distance of 4 mm with a piston having a cross-sectional area of 1 cm$^2$. The average gel rigidity values with respect to various oil concentrations are set forth in Table II below.

TABLE II

| Oil per 100 parts of Triblock copolymer | Gel Rigidity, gram Bloom |
|---|---|
| 360 | 500 |
| 463 | 348 |
| 520 | 280 |
| 615 | 240 |
| 635 | 220 |
| 710 | 172 |
| 838 | 135 |

TABLE II-continued

| Oil per 100 parts of Triblock copolymer | Gel Rigidity, gram Bloom |
|---|---|
| 1,587 | 54 |

EXAMPLE III

Example II was repeated except about 980 parts oil was used and the gel rigidity found to be about 101 gram Bloom. Other properties measured were: tensile strength at break about $4.4 \times 10^6$ dyne/cm$^2$, elongation at break about 2,470%, elasticity modulus about $3.5 \times 10^4$ dyne/cm$^2$, and shear modulus about $3.7 \times 10^4$ dyne/cm$^2$. The tensile strength, elongation, elasticity modulus were measured with cross-head separation speed of 25 cm/minute at room temperature. The shear modulus was measured with a 1, 2, and 3 kilogram load at room temperature.

EXAMPLE IV

Example II was repeated except about 520 parts of a polybutene (Amoco Indopol H-300) was used and the gel rigidity found to be about substantially unchanged with respect to use of naphthenic oil alone.

EXAMPLE V

Example II was repeated except about 520 parts of a polypropene (Amoco C-60) was used and the gel rigidity found to be about substantially unchanged with respect to use of naphthenic oil alone.

EXAMPLE VI

Example II was repeated except about 520 parts of a polyterpene (Hercules Piccolyte S 10) was used and the gel rigidity found to be about substantially unchanged with respect to use of naphthenic oil alone.

EXAMPLE VII

Example II was repeated except about 360 parts of a combined mixure of: 72 parts of a paraffinic oil (ARCO prime 200), 72 parts of a naphthenic oil (ARCO Tufflo 6014), 72 parts of a polybutene oligomer (Amoco Indopol H-200), 72 parts of a polypropene oligomer (Amoco Polypropene C-60), and 72 parts of a polyterpene oligomer (Hercules Piccolyte S 10) was used and the gel rigidity found to be about substantially unchanged with respect to the use of naphthenic oil alone.

EXAMPLE VIII

Example III was repeated except 933 parts oil with 147 parts by weight of a poly(styrene-ethylene-butylene-styrene) triblock copolymer containing 47 parts of a naphthenic process oil (Shell Kraton G 4609) having a styrene to ethylene and butylene ratio of about 33:67 was used and the physical properties were found to be about substantially unchanged with respect to the components used in Example III.

EXAMPLE IX

Example III was repeated except 933 parts oil with 147 parts by weight of a poly(styrene-ethylene-butylene-styrene) triblock copolymer containing 47 parts of a paraffinic white petroleum oil (Shell Kraton G 4609) having a styrene to ethylene and butylene block ratio of about 33:67 was used and the physical properties were found to be substantially unchanged with respect to the components used in Example III.

EXAMPLE X

Example II was repeated except about 400 parts of oil was used and the properties measured were: tear propagation about $1.4 \times 10^6$ dyne/cm$^2$, no crack growth in 180° bend under 50 gram load for 5,000 hours at room temperature, tensile strength about $4 \times 10^6$ dyne/cm$^2$, elongation at break about 1,700% tensile set about 0% at 1,200% elongation, compression set about 0% when tested under 5,000 gram load for 24 hours, and 100% snap back recovery after extension to 1,200%.

Examples XI–XIV below illustates other modes of practice presently contemplated.

EXAMPLE XI

The procedure of Example II is repeated except a poly(styrene-ethylene-butylene-styrene) triblock copolymer is used having a styrene end block to ethylene and butylene center block ratio of about 32:68 and the gel rigidity is found to be about 20 to about 700 gram Bloom.

EXAMPLE XII

The procedure of Example II is repeated except a poly(styrene-ethylene-butylene-styrene) triblock copolymer is used having a styrene end block to ethylene and butylene center block ratio of about 34:66 and the gel rigidity is found to be about 20 to about 700 gram Bloom.

EXAMPLE XIII

The procedure of Example II is repeated except a poly(styrene-ethylene-butylene-styrene) triblock copolymer is used having a styrene end block to ethylene and butylene center block ratio of about 36:64 and the gel rigidity is found to be about 20 to about 700 gram Bloom.

EXAMPLE XIV

The procedure of Example II is repeated except a poly(styrene-ethylene-butylene-styrene) triblock copolymer is used having a styrene end block to ethylene and butylene center block ratio of about 38:62 and the gel rigidity is found to be about 20 to about 700 gram Bloom.

EXAMPLE XV

A sheet (3 cm × 28 cm × 43 cm) formed from the composition of Example III was placed in contact with a vertical concrete wall and objects such as ping pong balls, golf balls, and a common clay brick were thrown at it from a distance of about 4 meters. Upon striking the sheet, the various objects adhered to it and were not damaged by the impact.

EXAMPLE XVI

A raw (grade AA large size) hen egg was dropped from a height of about 8 meters on to a sheet (0.5 cm × 25 cm × 25 cm) formed from the composition of Example III which was expanded to about 5 times the original dimension. Upon striking the expanded sheet, the egg adhered to it and was not damaged.

EXAMPLE XVII

Compositions of Example II are poured into a planoconvex, a bi-convex, a converging meniscus, a planoconcave, a bi-concave, a diverging meniscous, a cylindrical, and a spherical lens forming container and allowed to cool to room temperature and removed. The resultant lenses are used to image news print.

EXAMPLE XVIII

Compositions of Example II are continuously extruded into 1 meter length rod shape articles through a 0.05, a 0.1, a 0.2, a 0.4, a 0.8, a 1.0, a 1.5, a 1.8, a 2.0, a 4.0, and a 8.0 cm (inside diameter) pipe. The extruded articles are allowed to cool to room temperature. Light from a Spectra Physics Model 155A laser with a wavelength of 632.8 nm is introduced at one end of each article and transmitted therethrough.

EXAMPLE XIX

Two plano-convex lenses of Example XVII are joined at their base forming a sphere. The resultant sphere is thrown against a hard smooth glass door and upon impact is deformed into the shape of a pancake; upon recovery back to the original shape of a sphere, it slowly roll down the surface of the door under the force of gravity. The lenses are again joined at their base with only half of the total base surface areas overlapping; the so joined lenses are thrown against a hard smooth glass door and upon recovery the lenses in union rolls down the surface of the door showing cam rolling action.

EXAMPLE XX

The lenses of Example XVII are deformed by two thin, rigid optical surface conforming sandwich sheets. The resulting deformed gelatious lenses are used to view news print and other objects.

What is claimed is:

1. A gelatinous elastomer composition consisting essentially of:
   (a) 100 parts by weight of triblock copolymer of the general configuration poly(styrene-ethylene-butylene-styrene) wherein said styrene end block to ethylene and butylene center block ratio is within the range of from between 31:69 to 40:60;
   (b) from about 300 to about 1,600 parts by weight of a plasticizing oil;
   (c) said gelatinous elastomer composition having a gel rigidity of about 20 gram to about 700 gram Bloom.

2. A gelatinous elastomer composition of claim 1, wherein said plasticizing oil is selected from the group consisting of petroleum paraffinic oils, petroleum naphthenic oils, and mixtures thereof.

3. A gelatinous elastomer composition of claim 1, wherein said plasticizing oil is selected from the group consisting of synthetic polybutene oils, synthetic polypropene oils, synthetic polyterpene oils and mixtures thereof.

4. A gelatinous elastomer composition of claim 1, wherein said plasticizing oil is selected from the group consisting of petroleum paraffinic oils, petroleum naphthenic oils, synthetic polybutene oils, synthetic polypropylene oils, synthetic polyterpene oils and mixtures thereof; said oils having an average molecular weight of between about 200 to about 700.

5. A gelatinous elastomer composition of claim 4, wherein said styrene end block to ethylene and butylene center block ratio is about 32:68 to about 38:62.

6. A gelatinous elastomer composition of claim 4, wherein said styrene end block to ethylene and butylene center block ratio is about 32:68 to about 36:64.

7. A gelainous elastomer composition of claim 4, wherein said styrene end block to ethylene and butylene center block ratio is about 32:68 to about 34:66.

8. A gelatinous elastomer composition of claim 2, wherein said oils having an average molecular weight of between about 200 to about 700.

9. A gelatinous elastomer composition of claim 3, wherein said oils having an average molecular weight of between about 200 to about 700.

10. A toy solid hemisphere article formed from a gelatinous elastomer composition according to claim 1 wherein said article exhibits high creep, craze, tear, and crack resistance and is substantially free from oil bleedout.

11. A flexible toy rod formed from a gelatinous elastomer composition according to claim 2 wherein said article exhibits high creep, craze, tear, and crack resistance and is substantially free from oil bleedout.

12. An article formed from a gelatinous elastomer composition according to claim 3.

13. A cladding for optical fiber made from a gelatinous elastomer composition according to claim 4 wherein said article exhibits high creep, craze, tear, and crack resistance and is substantially free from oil bleedout.

14. A prism formed from a gelatinous elastomer composition according to claim 7 wherein said article exhibits high creep, craze, tear, and crack resistance and is substantially free from oil bleedout.

15. A gelatinous elastomer composition of claim 1, wherein said styrene end block to ethylene and butylene center block ratio is about 32:68 to about 38:62.

16. A gelatinous elastomer composition of claim 1, wherein said styrene end block to ethylene and butylene center block ratio is about 32:68 to about 36:64.

17. A gelatinous elastomer composition of claim 1, wherein said styrene end block to ethylene and butylene center block ratio is about 32:68 to about 34:66.

18. A article formed from a gelatinous elastomer composition according to claim 1 wherein said article exhibits high creep, craze, tear, and crack resistance and is substantially free from oil bleedout.

19. A article formed from a gelatinous elastomer composition according to claim 16 wherein said article exhibits high creep, craze, tear, and crack resistance and is substantially free from oil bleedout.

20. A article formed from a gelatinous elastomer composition according to claim 15 wherein said article exhibits high creep, craze, tear, and crack resistance and is substantially free from oil bleedout.

21. A transparent lens formed from a gelatinous elastomer composition of claim 1, 2, 3 or 4 wherein said article exhibits high creep, craze, tear, and crack resistance and is substantially free from oil bleedout.

22. A light conducting rod formed from a gelatinous elastomer composition according to claim 1, 2, 3, or 4 wherein said article exhibits high creep, craze, tear, and crack resistance and is substantially free from oil bleedout.

* * * * *